United States Patent [19]

Brusasco

[11] Patent Number: 5,129,898
[45] Date of Patent: Jul. 14, 1992

[54] PROSTHESIS FOR REDUCING AND LOCKING LIMB BONE FRACTURES

[75] Inventor: Enzo Brusasco, Turin, Italy

[73] Assignee: Roltra-Morse S.p.A., Rivoli, Italy

[21] Appl. No.: 534,944

[22] Filed: Jun. 8, 1990

[30] Foreign Application Priority Data

Jun. 9, 1989 [IT] Italy .................... 67468 A/89

[51] Int. Cl.$^5$ .............................................. A61F 5/04
[52] U.S. Cl. ........................................ 606/58; 606/56; 606/57; 623/16
[58] Field of Search ............... 623/16, 17; 606/63, 606/72, 53-59

[56] References Cited

U.S. PATENT DOCUMENTS

| 2,502,902 | 4/1950 | Tofflemire | 606/57 X |
| 3,977,397 | 8/1976 | Kalnborz et al. | 606/56 X |
| 4,628,922 | 12/1986 | Dewar | 606/59 X |
| 4,643,177 | 2/1987 | Sheppard et al. | 606/55 X |
| 4,936,843 | 6/1990 | Sohngen | 606/56 X |

FOREIGN PATENT DOCUMENTS

| 0314021 | 5/1989 | European Pat. Off. | 606/54 |
| 0888970 | 12/1981 | U.S.S.R. | 606/57 |
| 0921546 | 4/1982 | U.S.S.R. | 606/56 |

Primary Examiner—David J. Isabella
Assistant Examiner—David H. Willse
Attorney, Agent, or Firm—Klauber & Jackson

[57] ABSTRACT

A prosthesis comprising two tubular brackets connected in sliding manner and securable by means of pins to the ends of the fractured bone. The two brackets are connected by means of a flexible cable the ends of which the connected by a cable tensioning device. The cable is guided by a series of circumferential grooves arranged alternately on the two brackets, and is tightened by the cable tensioning device in such a manner as to exert, between the two brackets and in one operation, a traction or compression force evenly distributed along the brackets.

14 Claims, 4 Drawing Sheets

PROSTHESIS FOR REDUCING AND LOCKING LIMB BONE FRACTURES

BACKGROUND OF THE INVENTION

The present invention relates to a temporary prosthesis or appliance for the treatment of bone fractures in lieu of the traditional plaster cast technique.

Known prostheses employed in the treatment of bone fractures comprise two brackets, each secured to the end of one of the fractured bone portions. According to the known technique, once secured to the fractured bone, the brackets are connected to each other by means of separate ties or pins requiring individual adjustment.

Known prostheses of the aforementioned type present numerous drawbacks, foremost of which is that, instead of being preassembled, the component parts are assembled in loco with obvious discomfort to patients. Moreover, the use of ties with individual adjusters involves prolonged, complex adjustment of the traction and compression required for correctly reducing the fracture, which forces are not always evenly distributable along the brackets.

SUMMARY OF THE INVENTION

The aim of the present invention is to provide a prosthesis designed to overcome the above drawbacks. With this aim in view, according to the present invention, there is provided a prosthesis for reducing and locking limb bone fractures, said prosthesis comprising two brackets secured to the fractured bone on opposite sides of the fracture; and adjustable connecting means for connecting the brackets together; characterised by the fact that it also comprises guide means located on a first of said brackets and connected in siding manner to a second of said brackets for axially guiding said second bracket as it moves in relation to said first bracket; said connecting means comprising a flexible element of adjustable length extending between said two brackets in a substantially fret type pattern and connected in sliding manner to each said bracket.

Said flexible element preferably comprises a flexible cable and a cable tensioning device for connecting the opposite ends and adjusting the length of said cable.

Clearly, therefore, the above prosthesis is fully preassembled and, by simply adjusting the length of the flexible element, preferably by means of the cable tensioning device, the tension of the flexible element is automatically distributed evenly over the circumference of the two brackets.

BRIEF DESCRIPTION OF THE DRAWINGS

A number of non-limiting embodiments of the present invention will be described by way of example with reference to the accompanying drawings, in which.

DETAILED DESCRIPTION OF THE INVENTION

Figure 2:
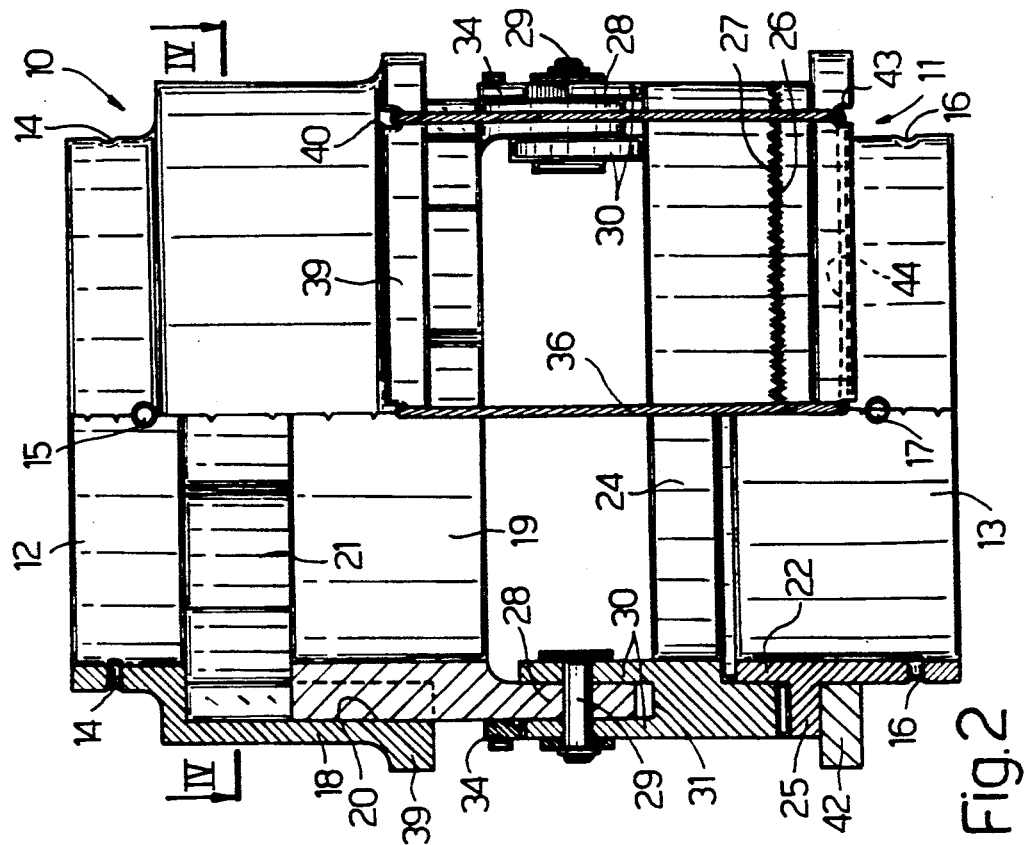
FIG. 2 shows a partially-sectioned side view of the FIG. 1 prosthesis.
Figure 1:
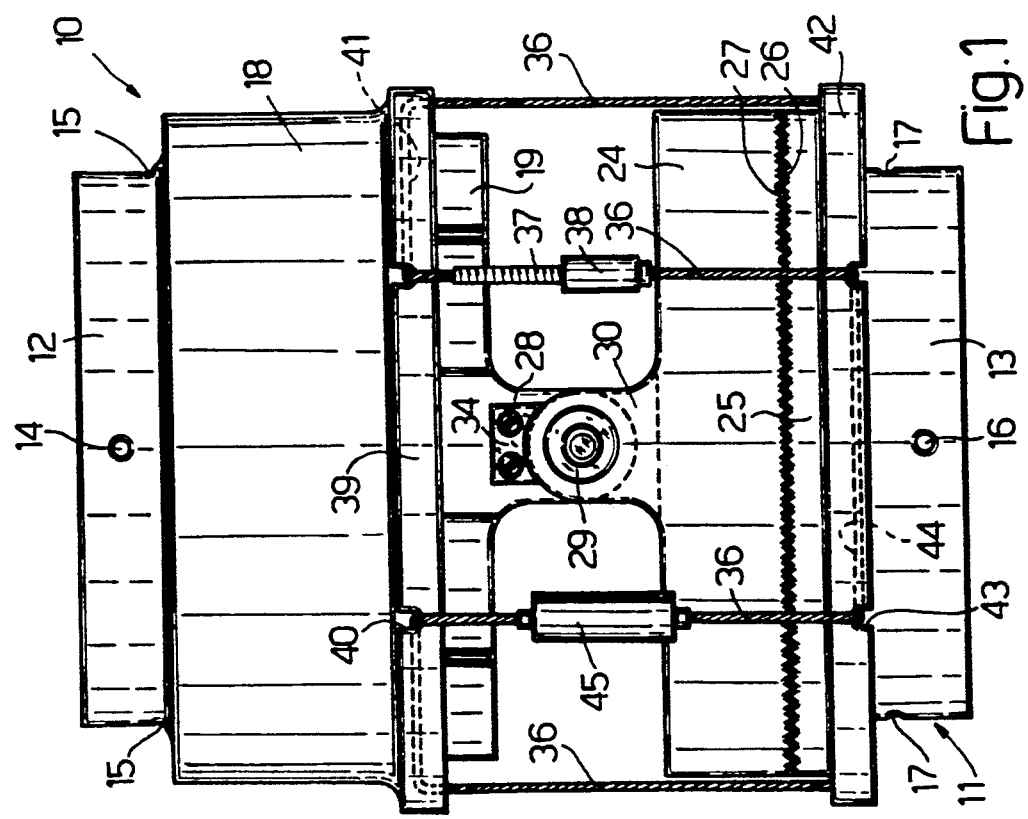
FIG. 1 shows an external view of a prosthesis for reducing and locking limb bone fractures, according to a first embodiment of the present invention.

As shown in FIGS. 1 and 2, the temporary prosthesis for reducing and locking bone fractures according to the present invention substantially comprises two substantially tubular brackets 10 and 11 for enclosing the fractured limb. In particular, brackets 10 and 11 present respective annular portions 12 and 13, the inside diameters of which are sized according to the size of the limb in question.

Each bracket 10 and 11 is designed to fit on to the end of one of the two fractured bone portions. For this purpose, portion 12 of bracket 10 presents two pairs of diametrical holes 14 and 15 designed to receive two pins fitted through one of the two fractured bone portions, for securing bracket 10 to the same. Similarly, portion 13 of bracket 11 presents a further two pairs of diametrical holes 16 and 17 for securing bracket 11 to the other fractured bone portion by means of a further two through pins.

Said two pairs of holes 14, 15 and 16, 17 on the respective portions of brackets 10 and 11 are located in two perpendicular, diametrical planes, and in two different planes perpendicular to the bracket axis.

Figure 4:
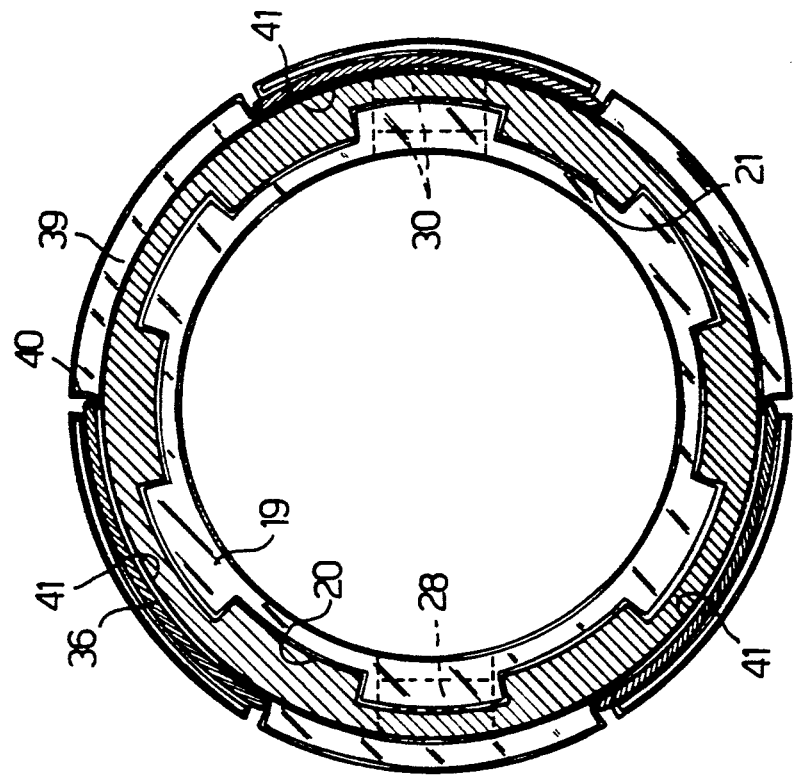
FIG. 4 shows a section along line IV—IV in FIG. 2.

Bracket 10 also comprises a portion 18 larger in diameter than portion 12 and mounted so as to slide axially over a tubular member or sleeve 19. For this purpose, the outer surface of sleeve 19 presents a series of equally-spaced prismatic axial grooves 20 (FIG. 4) engaged by a series of mating ribs 21 on the inner surface of portion 18 of bracket 10.

Bracket 11 (FIGS. 1 and 2) presents a further portion 22 designed to engage an offset inside a ring 24. For this purpose, bracket 11 presents an integral flange 25, the surface of which facing bracket 10 presents a finely knurled or toothed portion 26 designed to engage a mating knurled or toothed portion 27 on the front edge (bottom edge in the drawing) of ring 24. Bracket 11 may thus be fitted on to ring 24 in various angular positions, for mutually positioning hole pairs 14, 15 and 16, 17 as required for the type of fracture in question.

Figure 5B:
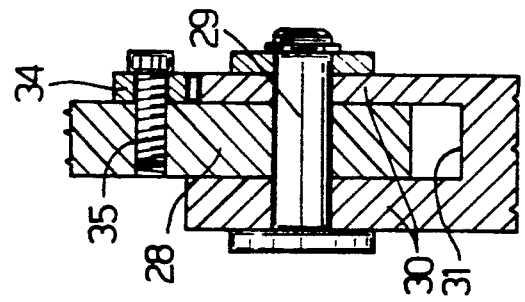
FIG. 5b is a longitudinal cross-section view of the portion of the prosthesis of FIB. 5a, FIG. 6 shows a partially-sectioned external view of a further embodiment of the prosthesis according to the present invention.

Sleeve 19 presents two drilled, diametrically-opposed, downward-facing appendixes 28 pivoting on two diametrical pins 29 on two drilled appendixes 30 of ring 24. In particular, each appendix 30 presents a groove 31 (FIG. 5b) for receiving a corresponding drilled appendix 28, so that pin 29 may be inserted inside the holes on appendixes 30 and 28 and secured to appendix 30 in known manner, e.g. by means of a washer and flexible bracket.

Figure 3:
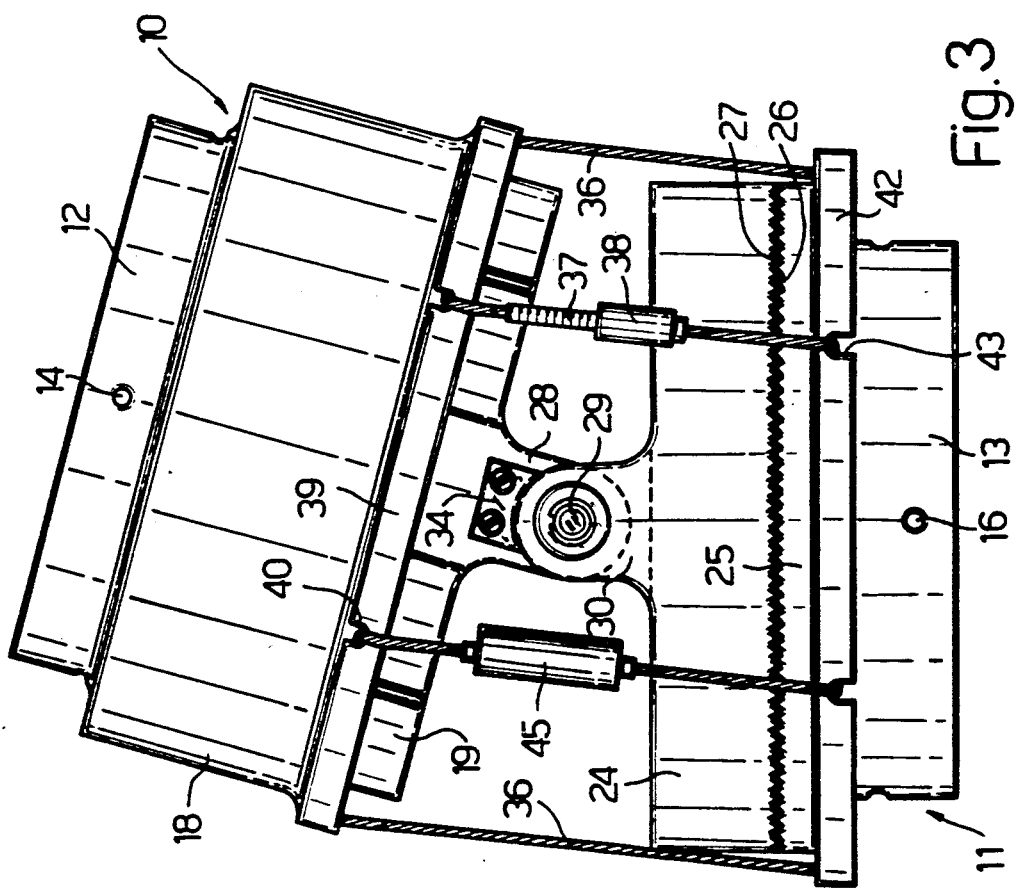
FIG. 3 shows an external view of the FIG. 1 prosthesis in a different operating position.
Figure 5A:
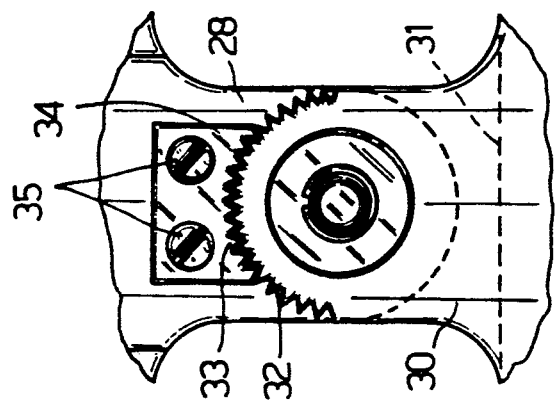
FIG. 5a shows a larger-scale section of a detail on the prosthesis according to the present invention.

The top outside edge of each appendix 30 presents a knurled portion 32 (FIG. 5a) engaged by a mating knurled edge 33 of a plate 34. Said plate 34 is secured by two screws 35 to the respective appendix 28 of sleeve 19 (FIGS. 1 and 2), so that the respective axes of brackets 10 and 11 may be positioned angularly as required by the fracture, e.g. as shown in FIG. 3. Sleeve 19 may then be locked on to pins 29 in the selected angular position, by securing plate 34 by means of screws 35 to appendix 28.

Brackets 10 and 11 are connected via adjustable connecting means comprising a flexible cable 36, e.g. a plastic-coated stranded steel cable, or a synthetic fibre or carbon cable. The two ends of cable 36 are connected by a cable tensioning device consisting of a screw 37 secured to one end of cable 36, and a nut screw 38 connected in rotary manner to the other end of cable 36.

For guiding cable 36, bracket 10 presents a flange 39 divided into an even number of sectors by equally-spaced axial grooves 40.

Half of each alternate sector on flange 39 presents a circumferential groove 41 in which to wind and guide cable 36, and located on the surface of flange 39 facing outwards of the prosthesis (upwards in FIGS. 1 and 2).

Bracket 11 presents an annular flange 42 resting on the shoulder formed by flange 25 and divided into the same number of sectors as flange 39 by a series of equally-spaced axial grooves 43. Half of each alternate sector on flange 42 presents a circumferential groove 44 on the surface of flange 42 facing downwards in FIGS. 1 and 2.

Regardless of the angular position of bracket 11 in relation to ring 24 and, consequently, bracket 10, flange 42 is positioned angularly on bracket 11 so that the sectors of flange 42 featuring groove 44 re aligned with those of flange 39 having no groove 41. Grooves 43 on flange 42 are thus aligned with grooves 40 on flange 39. Cable 36 is wound alternately inside a groove 41 on flange 39 and a groove 44 on flange 42, so as to form, between pairs of grooves 40 and 43, a fret type pattern of cable portions substantially parallel to the axes of brackets 10 and 11. Cable tensioning device 37, 38 is advantageously located between one of said pairs of grooves 40, 43, which thus constitute a number of equally-spaced positions in which brackets 10 and 11 are connected about their respective circumferences.

Cable 36 is also provided with a tension gauge 45, e.g. a dynamometric gauge, comprising an optical tension indicator.

Brackets 10 and 11, sleeve 19, ring 24 and flange 42 are made of rigid, sufficiently lightweight material, preferably plastic, for minimising discomfort to the patient.

The prosthesis as described above is thus fitted fully preassembled on to the fractured limb, with the exception of plate 34, which is assembled later on, and with cable 36 wound loosely so as to keep connections 32–33 and 26–27 open. Portion 12 of bracket 10 is then secured to a first portion of the fractured bone, at which point, plate 34 is assembled for mutually securing brackets 10 and 11 in the required angular position, and bracket 11 is turned about is axis in relation to ring 24, so as to position holes 16 and 17 as required, and then secured to the other fractured bone portion. Finally, cable tensioning device 37, 38 is operated for closing connection 26–27 and, at the same time, exerting the required compression between brackets 10 and 11, which compression is distributed evenly about the perimeter of brackets 10 and 11 and monitored continually on gauge 45.

Figure 6:
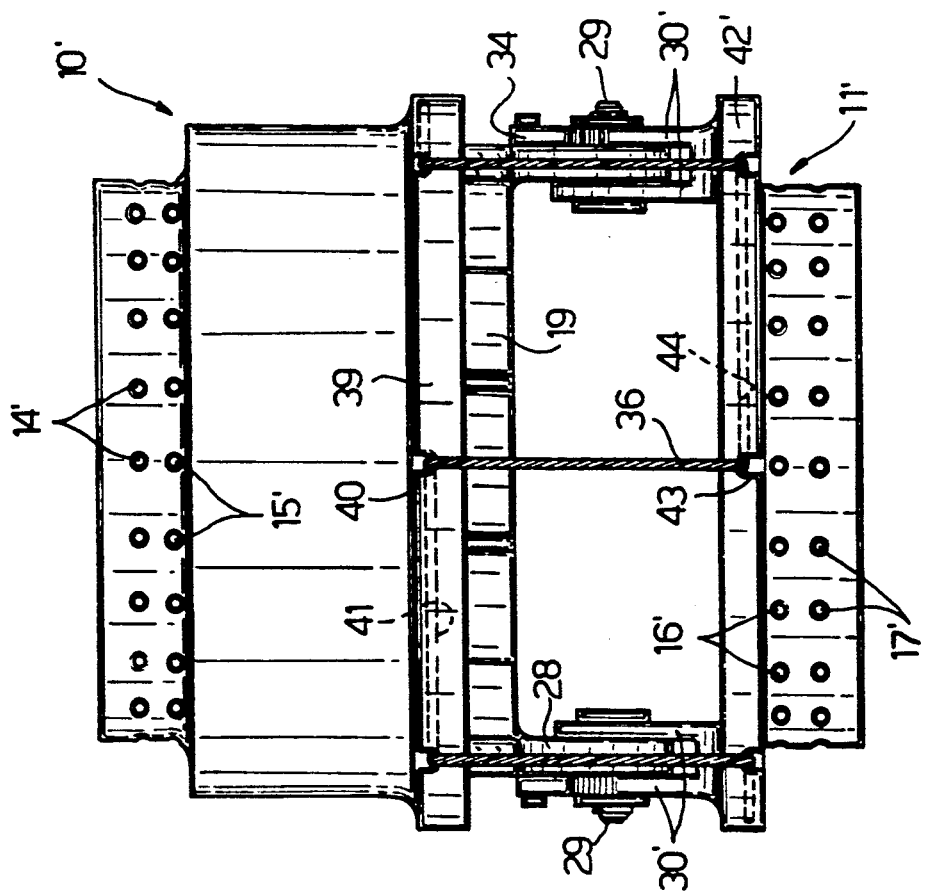

FIG. 6 shows a further embodiment of the prosthesis according to the present invention, wherein slidable top bracket 10' presents two series of diametrically-opposed hole pairs 14' and 15' located in different planes perpendicular to the axis of bracket 10'. Similarly, bottom bracket 11' presents two series of diametrically-opposed hole pairs 16' and 17' located in different planes perpendicular to the axis of bracket 11'.

The two fractured bone portions may be pinned using one or two pins for each bracket 10', 11', and selecting appropriate hole pairs 14', 15', 16' and 17', in which case, mutual angular positioning of brackets 10' and 11' is no longer required. Bracket 11' is therefore formed in one piece with two appendixes 30' supporting pins 29, thus enabling ring 24 in FIGS. 1 to 3 and the two knurled portions 26, 27 to be dispensed with.

Bracket 11' (FIG. 6) is also formed in one piece with a flange 42' featuring grooves 43 and 44 for cable 36, which are thus correctly related at all times to grooves 40 and 41 on bracket 10'. All the other components on the prosthesis are the same as in FIGS. 1 to 3, including cable tension device 37, 38 and tension gauge 45, which are not shown in FIG. 6.

The FIG. 6 prosthesis is fitted to and removed from the limb by releasing cable 36 from grooves 41 and 44 and detaching flange 10' from sleeve 19.

Figure 7:
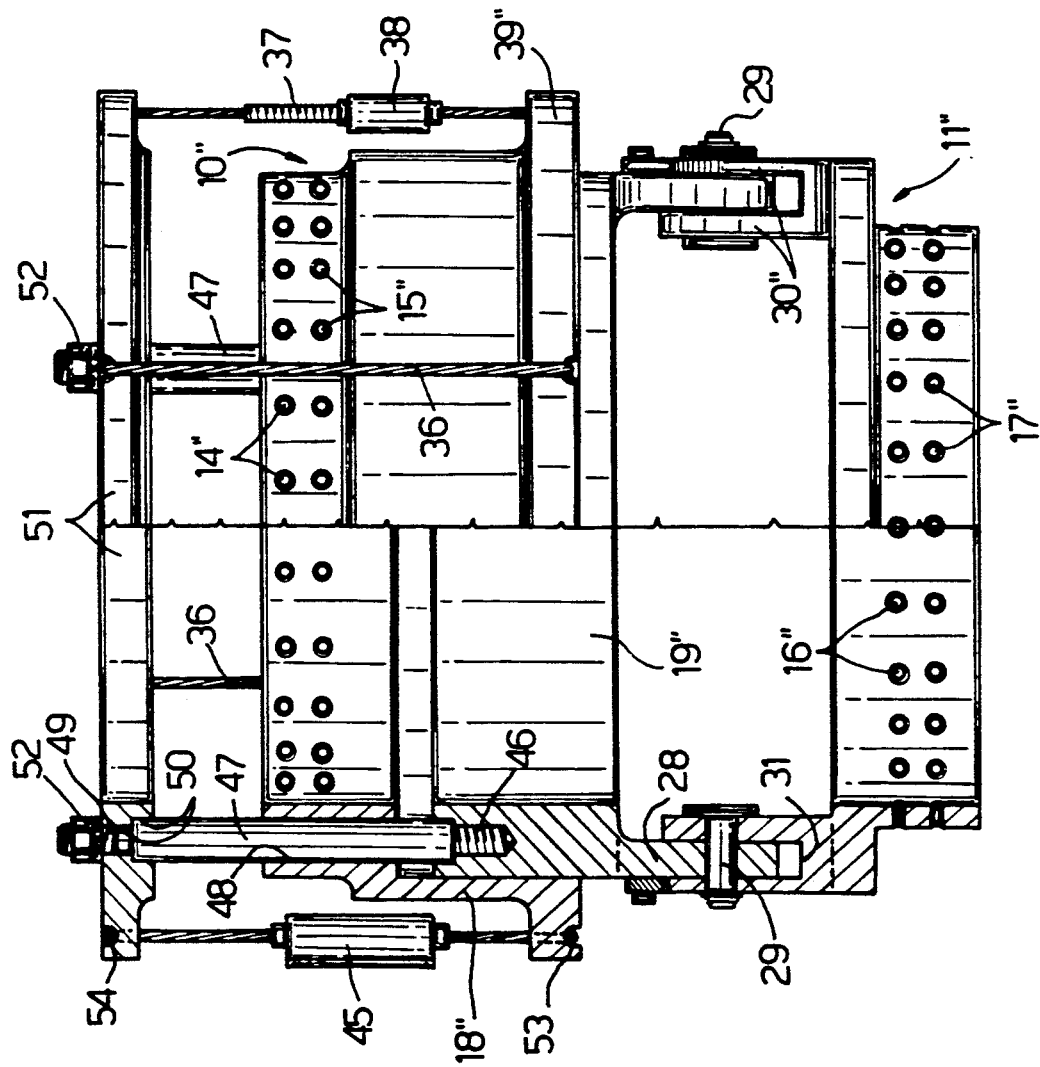
FIG. 7 shows an external view of a further embodiment of the prosthesis according to the present invention.

FIG. 7 shows a further embodiment of the present invention wherein brackets 10" and 11" present respective series of hole pairs 14", 15" and 16", 17" located in two planes as in FIG. 6 embodiment. The FIG. 7 prosthesis is designed to reduce the fracture by separating brackets 10" and 11" by means of the tension of cable 36.

For this purpose, the top edge of sleeve 19" presents three threaded axial holes into each of which is screwed the threaded end 46 of a respective pin 47 parallel to the axis of sleeve 19". Bracket 10" in turn presents three axial holes 48 engaged by said three pins 47, which thus provide for axially guiding bracket 10" as it moves in relation to sleeve 19". For guiding portion 18" of bracket 10", sleeve 19" therefore presents a cylindrical as opposed to a grooves surface.

On the end opposite threaded end 46, each pin 47 presents a threaded portion 49 engaged by a respective hole 50 on an annular flange 51 secured rigidly to pin 47 by means of three nuts 52 screwed on to threaded portions 49.

Cable 36 is guided, on one side, by a series of grooves 53 formed on the bottom surface of flange 39" on bracket 10" and arranged in the same way as grooves 41 on the prostheses in FIGS. 1 to 4 and FIG. 6, and, on the other, by a series of grooves 54 complementary to grooves 53 and formed on the top outside surface of flange 51.

Finally, tension gauge 45 is located on an axial portion of cable 36, not adjacent to that of tensioning device 37, 38. The indicator of gauge 45 may still be controlled visually, however, during operation of device 37, 38. When tensioning device 37, 38 is operated, cable 36 provides, in this case, for parting brackets 10" and 11" and so reducing overlapping bone fractures.

To those skilled in the art it will be clear that changes and improvements may be made to the prostheses as described and illustrated herein without, however, departing from the scope of the present invention. For example, the cable tensioning device may be operated by means of a knob. Locking of the mutual angular position of the brackets on pins 29 may be achieved by various, i.e. lever-operated, means. Finally, the prosthesis may also be employed by veterinarians for reducing animal bone fractures.

I claim:

1. A prosthesis for reducing and locking limb bone fractures, said prosthesis comprising two brackets (10, 11; 10', 11'; 10", 11") adapted to be secured to a fractured bone on opposite sides of the fracture; and adjustable connecting means for connecting the brackets together; characterised by the fact that said prosthesis also comprises guide means (19, 20; 19", 48) located on a first of said brackets (10, 11; 10', 11'; 10"; 11") and connected in sliding manner to a second of said brackets (10, 11; 10', 11'; 10", 11") for axially guiding said second bracket as it moves in relation to said first bracket; said connecting means comprising a flexible element (36, 37, 38) of adjustable length extending between said two brackets (10, 11; 10', 11'; 10", 11") in a substantially fret type pattern and connected in sliding manner to each said bracket (10, 11; 10', 11'; 10", 11").

2. A prosthesis as claimed in claim 1, characterised by the fact that said flexible element (36, 37, 38) comprises a flexible cable (36) and a cable tensioning device (37, 38) for connecting opposite ends of said flexible cable, and adjusting the length of said cable (36).

3. A prosthesis as claimed in claim 2, characterised by the fact that each said bracket (10, 11; 10', 11'; 10", 11") presents a series of circumferential grooves (41, 44; 53, 54) in which to wind and guide said cable (36); each said groove extending between two adjacent positions (40, 43) of a plurality of positions, and said grooves being formed on two flanges (39, 42'; 39", 51) of said brackets and alternating in such a manner as to arrange said cable in said substantially fret type pattern.

4. A prosthesis as claimed in claim 2, characterised by the fact that said cable tensioning device (37, 38) presents a gauge (45) for measuring the tension of said cable (36); said cable tensioning device and said gauge being located on two substantially parallel cable portions of said fret pattern.

5. A prosthesis as claimed in claim 4, characterised by the fact that said cable (36) is a plastic-coated stranded steel cable, and that said cable tensioning device (37, 38) consists of a screw (37) secured to one end of said cable, and a nut screw (38) connected in rotary manner to the other end of said cable.

6. A prosthesis as claimed in claim 1, characterised by the fact that each said bracket (10, 11; 10', 11'; 10", 11") presents two pairs of diametrical holes (14, 15; 16, 17) located in two diametrical planes perpendicular to each other but offset axially; each pair of holes being designed to receive a pin fitted through a respective fractured bone portion.

7. A prosthesis as claimed in claim 1, characterised by the fact that each said bracket (10', 11'; 10", 11") presents two series of diametrical hole pairs (14'-17'; 14"-17") located in two different planes perpendicular to the axis of said bracket; each pair of holes being designed to receive a pin fitted through a respective fractured bone portion.

8. A prosthesis as claimed in claim 1, characterised by the fact that said guide means (19, 20; 19", 47) are carried on a structure (19, 28; 24, 30; 19, 28, 30'; 19", 28, 30") comprising a sleeve (19, 19") on which said first bracket (10, 10', 10") slides axially; said sleeve pivoting on a pair of diametrical pins (29) integral with the other (11, 11', 11") of said brackets; and lock means (34) being provided for locking said sleeve in a given angular position in relation to said other bracket.

9. A prosthesis as claimed in claim 8, characterised by the fact that each said diametrical pin (29) is carried on an appendix (30, 30', 30") having a semicircular profile (32) facing said sleeve, the semicircular profile of at least one of said appendixes being knurled; said lock means comprising a plate (34) associated with said appendix and having a knurled profile (33) complementary to said knurled profile (3); and said plate (34) being secured in removable manner to said sleeve (19, 19").

10. A prosthesis as claimed in claim 8, characterised by the fact that the outer surface of said sleeve (19) presents a series of equally-spaced prismatic axial grooves (20) cooperating with a series of complementary ribs (21) on the inner surface of said first bracket (10, 10').

11. A prosthesis as claimed in claim 8, characterised by the fact that said sleeve (19") presents a series of pins (47) parallel to the axis of said sleeve and cooperating with a series of axial holes (48) on said first bracket (10").

12. A prosthesis as claimed in claim 10, characterised by the fact that said pair of diametrical pins (29) is carried on a ring (24) connectable to said other bracket (10) in a number of different angular positions; said ring (24) presenting a knurled front edge (26) connectable to a complementary knurled edge (27) on said other bracket (11).

13. A prosthesis as claimed in claim 3, characterised by the fact that a first (41) of said series of circumferential grooves is formed on a flange (39) formed in one piece with said first bracket (10), whereas the other series (44) of said circumferential grooves is formed on a flange (42) coaxial with said other bracket (11) and designed to turn about its axis for mutually phasing said two series of grooves (41, 44); said series of grooves (41, 44) being so formed on said flanges (39, 42; 38, 42') that, when said cable (36) is tightened, said brackets (10, 11; 10', 11') are brought closer together.

14. A prosthesis as claimed in claim 3, characterised by the fact that a first (53) of said series of circumferential grooves (53, 54) is formed on a flange (39") formed in one piece with said first bracket (10"), whereas the other series (54) of said circumferential grooves is formed on a flange (51) secured to a series of pins (47) in such a manner that, when said cable (36) is tightened, said brackets (10", 11") are parted.

* * * * *